US006656452B1

(12) United States Patent
Zapol et al.

(10) Patent No.: US 6,656,452 B1
(45) Date of Patent: Dec. 2, 2003

(54) USE OF INHALED NO AS ANTI-INFLAMMATORY AGENT

(75) Inventors: Warren M. Zapol, Concord, MA (US); Kenneth D. Bloch, Brookline, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 08/971,003

(22) Filed: Nov. 14, 1997

Related U.S. Application Data

(60) Provisional application No. 60/062,926, filed on Oct. 21, 1997.

(51) Int. Cl.$^7$ .............................. A61K 9/12; A61K 9/72

(52) U.S. Cl. .......................... 424/45; 424/46; 424/94.4; 514/611; 514/357; 514/226.5; 128/200.14; 128/200.23

(58) Field of Search ......................... 424/45, 46, 94.4; 514/611, 357, 226.5; 128/200.14, 200.23

(56) References Cited

U.S. PATENT DOCUMENTS

| | | | |
|---|---|---|---|
| 5,396,882 A | | 3/1995 | Zapol .................... 128/200.14 |
| 5,427,797 A | * | 6/1995 | Frostell et al. .............. 424/434 |
| 5,485,827 A | * | 1/1996 | Zapol et al. ........... 128/200.14 |
| 5,536,241 A | | 7/1996 | Zapol ......................... 604/23 |
| 5,570,683 A | * | 11/1996 | Zapol .................... 128/200.14 |
| 5,703,073 A | * | 12/1997 | Garvey et al. ............ 514/226.5 |
| 5,725,492 A | * | 3/1998 | Igo et al. ........................ 604/4 |
| 5,823,180 A | | 10/1998 | Zapol .................... 128/200.24 |
| 5,885,621 A | | 3/1999 | Head et al. ................. 424/718 |
| 6,063,407 A | | 5/2000 | Zapol et al. ................ 424/718 |

FOREIGN PATENT DOCUMENTS

| | | |
|---|---|---|
| EP | 0 692 984 B1 | 1/1996 |
| WO | WO 95/10315 | 4/1995 |
| WO | WO 95/12394 | 5/1995 |
| WO | WO 96/11688 | 4/1996 |

OTHER PUBLICATIONS

Chetham et al., "Inhale Nitric Oxide Pretreatment But Not Post–treatment Attenuates Ischemia–Reperfusion–induced Pulmonary Microvascular Leak", Anesthesiology 86:895–902, 1997.
Chintala et al., "Cyclic GMP But Not Cyclic AMP Prevents Renal Platelet Accumulation After Ischemia–Reperfusion in Anesthetized Rats", The Journal of Pharmacology & Exper Therapeutics 271:1203–1208, 1994.
Chollet–Martin et al., "Alveolar Neutrophil Functions and Cytokine Levels in Patients with the Adult Respiratory Distress Syndrome . . . ", Am. J. Respir. Crit Care Med. 153:985–990, 1996.
Gotuaco et al., "Inhaled Nitric Oxide Reduces Lung Inflammation in Rats Exposed To 100% Oxygen", Journal of Investigative Medicine, Southern Regional Meeting 45:68A, 1997.
Guidot et al., "Inhaled Nitric Oxide Prevents Neutrophil–mediated, Oxygen Radical–dependent Leak in Isolated Rat Lungs", American Journal of Physiology 269:L2–L5, 1995.
Guidot et al., "Inhaled NO Prevents IL–1–induced Neutrophil Accumulation and Associated Acute Edema in Isolated Rat Lungs", American Journal of Physiology 271:L225–L229, 1996.
Iadecola, "Bright and Dark Sides of Nitric Oxide in Ischemic Brain Injury", Trends Neurosci 20:132–139, 1997.
Johnson et al., "Cardioprotective Effects of Authentic Nitric Oxide in Myocardial Ischemia With Reperfusion", Critical Care Medicine 19:244–252, 1991.
Lee et al., "Chronic Inhalation of Nitric Oxide Inhibits Neointimal Formation After Balloon–Induced Arterial Injury", Circulation Research 78:337–342, 1996.
Schmidt et al., "NO at Work"K, Cell 78:919–925, 1994.
Trapani et al., "Hemodynamic Basis for the Depressor Activity of Zaprinast, A Selective Cyclic GMP Phosphodiesterase Inhibitor", The Journal of Pharmacology & Exper Therapeutics 258:269–274, 1991.
Werner et al., "Differing Roles of Nitric Oxide in the Pathogensis of Acute Edematous Versus Necrotizing Pancreatitis", Surgery 121:23–30, 1997.
Holmes, David R., Jr. et al., Contemporary Reperfusion Therapy for Cardiogenic Shock: The GUSTO–I Trial Experience; JACC, vol. 26, No. 3, pp. 668–674, 1995.
Foubert et al., "Safety Guidelines for use of Nitric Oxide" Lancet 339: 1615–1616 (1992).
Frostell et al., "Inhaled Nitric Oxide. A Selective Pulmonary Vasodilator Reversing Hypoxic Pulmonary Vasoconstriction" Circulation 83(6):2038–2047 (1991).
Groves et al., "Exogenous Nitric Oxide Inhibits in Vivo Platelet Adhesion Following Balloon Angioplasty" Cardiovasc Res 26(6): 615–619 (1992).
Harrison, "Endothelial Modulation of Vascular Tone: Relevance to Coronary Angioplasty and Restenosis" J Am Coll Cardiol. 17(6 Suppl B):71B–76B (1991).

(List continued on next page.)

Primary Examiner—Michael G. Hartley
Assistant Examiner—Mina Haghighatian
(74) Attorney, Agent, or Firm—Fish & Richardson P.C.

(57) ABSTRACT

A method for lessening or preventing non-pulmonary ischemia-reperfusion injury or inflammation in a mammal by identifying a mammal which has ischemia-reperfusion or is at risk for developing ischemia-reperfusion in a non-pulmonary tissue; and causing the mammal to inhale a therapeutically effective amount of gaseous nitric oxide sufficient to diminish the ability of leukocytes or platelets to become activated in a manner that contributes to an inflammatory process at the site of the ischemia-reperfusion or inflammation in the non-pulmonary tissue, thereby lessening or preventing non-pulmonary ischemia-reperfusion injury in the mammal.

16 Claims, No Drawings

OTHER PUBLICATIONS

Head et al., "Low Concentrations of Nitric Oxide Increase Oxygen Affinity of Sickle Erythrocytes In Vitro and In Vivo" *J Clin. Invest.* 100(5):1193–98 (1997).

Högman et al., "Prolonged Bleeding Time During Nitric Oxide Inhalation in the Rabbit" *Acta Physiol. Scand* 151:125–29 (1994).

Ichinose et al., "Prolonged Duration of Action of Inhaled Nitric Oxide by the cGMP Phosphodiesterase Inhibitor Zaprinast in Awake Lambs" *Anesthesiology* 81(3A):A640 (1994).

Ignarro, "Endothelium–Derived Nitric Oxide: Actions and Properties" *FASEB J.1* 3:31–36 (1989).

Ignarro, "Endothelium–Derived Nitric Oxide: Pharmacology and Relationship to the Actions of Organic Nitrate Esters" *Pharmaceutical Research* 6(8):651–59 (1989).

Lee et al., "Cellular and Molecular Mechanisms of Coronary Artery Restenosis" *Coron Artery Dis.* 4(3):254–59 (1993).

Radomski et al., "The Anti–Aggregating Properties of Vascular Endothelium: Interactions Between Prostacyclin and Nitric Oxide" *Br. J. Pharmac.* 92 639–46 (1987).

Rossaint et al., "Inhaled Nitric Oxide for the Adult Respiratory Distress Syndrome" *N Engl J Med.* 328(6):399–405 (1993).

Sellden et al., "Inhalation of Nitric Oxide Reduced Pulmonary Hypertension After Cardiac Surgery in a 3.2–kg Infant" *Anesthesiology* 78(3):577–80 (1993).

Stamler et al., "S–Nitrosylation of Proteins with Nitric Oxide: Synthesis and Characterization of Biologically Active Compounds" *Proc. Natl. Acad. Sci, USA* 89:444–48 (1992).

Wennmalm, "Nitric Oxide (NO) in the Cardiovascular System: Role in Atherosclerosis and Hypercholesterolemia" *Blood Press.* (5):279–82 (1994).

* cited by examiner

USE OF INHALED NO AS ANTI-INFLAMMATORY AGENT

CROSS REFERENCE TO RELATED APPLICATION

This application claims benefit from provisional application Ser. No. 60/062,926 filed Oct. 21, 1997.

STATEMENT AS TO FEDERALLY SPONSORED RESEARCH

Work on this invention was supported, in part, with funds from the United States government (USPHS grants HL66377, HL42397, and HL45895). The government therefore has certain rights in the invention.

FIELD OF THE INVENTION

The field of the invention is treatment of ischemia-reperfusion injury and inflammation.

BACKGROUND OF THE INVENTION

Nitric oxide (NO) is a cell membrane-permeable, free radical molecule which accounts for the vasodilator activity of endothelium-derived relaxing factor (reviewed in Schmidt et al., Cell 78:919–925 [1994]). NO interacts with several intracellular molecular targets, one of which is soluble guanylate cyclase (sGC). Binding of NO to the heme group in sGC stimulates the conversion of guanosine triphosphate (GTP) to guanosine-3',5'-cyclic monophosphate (cGMP). cGMP exerts it effects on cells, in part, through its action on cGMP-dependent protein kinase (cGDPK). Additional cGMP targets include cGMP-gated ion channels and cGMP-regulated cyclic nucleotide phosphodiesterases. Phosphodiesterases (PDEs) inactivate cGMP by converting it to GMP. At least four types of PDEs appear to participate in the metabolism of cyclic nucleotides in non-ocular tissues (types 1–3 and 5), only one of which, type 5 (PDE5), is specific for cGMP metabolism. Several agents act as selective inhibitors of PDE5, including dipyridamole and Zaprinast™.

The biological effects of NO are also mediated by cGMP-independent mechanisms. NO can serve as an antioxidant, opposing the effect of superoxides. The antioxidant properties of NO appear to account for its ability to modulate proinflammatory activation of endothelial cells. NO may also react with superoxide to form peroxynitrite which may be responsible for the cellular toxicity associated with high levels of NO production.

NO decreases the adherence and aggregation of platelets exposed to a variety of stimuli. This has been demonstrated in vitro and in vivo (Adrie et al., Circulation 94:1919–1926 [1996]). The effect of NO on platelet function appears to be mediated by cGMP and is augmented by PDE5 inhibitors (see PCT application WO96/25184, which is incorporated herein by reference).

The use of NO as a drug is complicated by evidence suggesting that high levels of NO can contribute to cell injury (Nicholson et al., Trends Pharmacol Sci 12:19–27 [1991]). This is, at least in part, mediated by the combination of NO with reactive oxygen intermediates to form peroxynitrite which decomposes to toxic $NO_2^+$ and $OH^-$. NO contributes to neuronal cell injury associated with cerebral ischemia (Iadecola, Trends Neurosci 20:132–139 [1997]). In addition, NO inhibits myocardial contractility and stimulates apoptosis of cardiac myocytes (Wu et al., J Biol Chem 272:14860–14866 [1997]), thereby impairing cardiovascular function. NO also contributes to inflammation in arthritis and possibly other autoimmune diseases when present at the site of inflammation (Nicholson et al., Id.).

NO inhibits adherence of neutrophils to endothelium, an effect which may depend on mast cells (Niu et al., Circ Res 79:992–999 [1996]).

SUMMARY OF THE INVENTION

It has been discovered that inhaled gaseous nitric oxide can act on both platelets and leukocytes, affecting them in a way that leaves them less likely to be activated once they reach a tissue susceptible to inflammation. The effect on platelets and leukocytes presumably occurs while they are in the pulmonary circulation, since NO itself is rapidly inactivated by hemoglobin once it contacts the blood (Rich et al., J Appl Physiol 75:1278–1284 [1993] and Rimar et al., Circulation 88:2884–2887 [1993]) and so likely does not travel to distal sites of inflammation.

Accordingly, the invention relates to a method for lessening or preventing non-pulmonary ischemia-reperfusion injury in a mammal. The method includes identifying a mammal (e.g., a human) that has ischemia-reperfusion or is at risk for developing ischemia-reperfusion in a non-pulmonary tissue, and causing the mammal to inhale a therapeutically effective amount of gaseous nitric oxide. This amount is sufficient to diminish the ability of circulating leukocytes or platelets to become activated and contribute to an inflammatory process at the site of ishemia-reperfusion in the non-pulmonary tissue. This lessens or prevents non-pulmonary ischemia-reperfusion injury in the mammal. In combination with the inhaled NO gas, the mammal can be administered a therapeutically effective amount of a second compound that potentiates the therapeutic effect of gaseous NO. The second compound can be, for example, a phosphodiesterase inhibitor (e.g., 2-o-propoxyphenyl-8-azapurin-6-one [Zaprinast™], dipyridamole, theophylline, sildenafil [Viagra™, Pfizer], or 1,3-dimethyl-6-[2-propoxy-5-methanesulphonylamidophenyl]-pyrazolo[3,4-D]pyrimidin-4-[5H]-one) or superoxide dismutase. The second compound can alternatively be an antithrombotic agent such as ticlopidine, streptokinase, urokinase, t-PA or an analog thereof (e.g., met-t-PA, Retevase™, or FE1X), heparin, hirudin or an analog thereof (e.g., Hurulog™), non-steroidal anti-inflammatory agent (e.g., indomethacin or aspirin), a glucocorticoid (e.g., prednisone), or a cytotoxic agent (e.g., methotrexate); or an anti-leukocyte agent such as an anti-leukocyte antibody.

The method is used to treat or prevent ischemia-reperfusion injury including those caused by surgery (e.g., transplantation surgery [especially kidney or heart transplantation surgery] or heart bypass surgery), thrombolysis, stroke, trauma-induced temporary hypotension, or a vascular interventional procedure such as atherectomy or angioplasty including the use of a laser, balloon, or stent. The method can be used to treat or prevent ischemia-reperfusion injury after percutaneous transluminal coronary angioplasty. The injury treated or prevented can occur in any non-pulmonary tissue, including the kidney, heart, or brain.

The invention also features a method for decreasing or preventing non-pulmonary inflammation in a mammal. Examples of non pulmonary inflamation are arthritis, myocarditis, encephalitis, transplant rejection, systemic lupus erythematosis, gout, dermatitis, inflammatory bowel disease, hepatitis, or thyroiditis. This method includes the steps of identifying a mammal which has existing inflammation or is at risk for developing inflammation in a non-pulmonary tissue; causing the mammal to inhale a therapeutically effective amount of gaseous nitric oxide sufficient to diminish the ability of circulating leukocytes or platelets to become activated in a manner that contributes to an inflammatory process in the non-pulmonary tissue, thereby decreasing or preventing non-pulmonary inflammation in the mammal; and administering to the mammal a therapeutically effective amount of a second compound that potentiates the anti-inflammatory effect of inhaled gaseous nitric oxide. The second compound can be a phosphodiesterase inhibitor (e.g., 2-o-propoxyphenyl-8-azapurin-6-one [Zaprinast™], dipyridamole, theophylline, sildenafil [Viagra™, Pfizer], or 1,3-dimethyl-6-[2-propoxy-5-methanesulphonylamidophenyl]-pyrazolo[3,4-D]pyrimidin-4-[5H]-one) or superoxide dismutase. The second compound can alternatively be an anti-inflammatory drug such as a non-steroidal anti-inflammatory agent (e.g., indomethacin or aspirin), a glucocorticoid (e.g., prednisone), or a cytotoxic agent (e.g., methotrexate).

The NO gas inhaled by the mammal in the method of this invention can be administered at a predetermined concentration. Preferably it is administered in the absence of tobacco smoke. Preferably the predetermined concentration is 0.1 ppm to 300 ppm, more preferably 1 ppm to 250 ppm, and most preferably 5 ppm to 200 ppm. NO can be inhaled continuously or intermittently for an extended period, i.e., for at least 24 hours.

As used herein "preventing" an injury means preventing at least part of the injury, and does not imply that 100% of the injury is prevented. Injury prevented is ischemia-reperfusion injury or inflammation. As used herein, injury "occurs spontaneously," means that the injury has no readily observable cause.

As used herein, "potentiating the therapeutic effect of gaseous nitric oxide," (by a second compound) means increasing the duration or magnitude of the effect.

As used herein, "vascular interventional procedure" means any surgical procedure that involves an anatomical disruption or a mechanical disturbance of a blood vessel.

Other features and advantages of the present invention will be apparent from the following detailed description and also from the claims.

DETAILED DESCRIPTION OF THE INVENTION

This invention relates to methods of treating or preventing ischemia-reperfusion injury or inflammation through inhalation of nitric oxide gas. The methods are simple and rapid, affect non-pulmonary tissues, and do not lead to NO-associated cytotoxicity in non-pulmonary tissues.

Without further elaboration, it is believed that one skilled in the art can, based on the above disclosure and the description below, utilize the present invention to its fullest extent. The following description is to be construed as merely illustrative of how one skilled in the art can treat or prevent ischemia-reperfusion injury or inflammation in non-pulmonary tissues using inhaled nitric oxide, and does not limit the remainder of the disclosure in any way. Any publications cited in this disclosure are hereby incorporated by reference.

Administration of Inhaled NO

Inhaled NO is preferably administered from a source of stored, compressed NO gas. Compressed NO gas may be obtained from a commercial supplier such as Ohmeda, typically as a mixture of 200–800 ppm NO in pure $N_2$ gas. The source of NO can be 100% NO, or diluted with $N_2$ or any other inert gas (e.g., helium). It is vital that the NO be obtained and stored as a mixture free of any contaminating $O_2$ or higher oxides of nitrogen, because such higher oxides of nitrogen (which can form by reaction of $O_2$ with NO) are potentially harmful to lung tissues. If desired, purity of the NO may be demonstrated with chemiluminescence analysis, using known methods, prior to administration to the patient. Chemiluminescence NO—$NO_x$ analyzers are commercially available (e.g., Model 14A, Thermo Environmental Instruments, Franklin, Mass.). The NO—$N_2$ mixture may be blended with air or $O_2$ through, for example, calibrated rotameters which have been validated previously with a spirometer. The final concentration of NO in the breathing mixture may be verified with a chemical or chemiluminescence technique well known to those in the field (e.g., Fontijin et al., Anal Chem 42:575 [1970]). Alternatively, NO and $NO_2$ concentrations may be monitored by means of an electrochemical analyzer. Any impurities such as $NO_2$ can be scrubbed by exposure to NaOH solutions, baralyme, or sodalime. As an additional control, the $FiO_2$ of the final gas mixture may also be assessed. Optionally, the ventilator can have a gas scavenger added to the expiratory outlet to ensure that significant amounts of NO do not escape into the adjacent environment.

In a hospital or emergency field situation, administration of NO gas can be accomplished, for example, by attaching a tank of compressed NO gas in $N_2$, and a second tank of oxygen or an oxygen/$N_2$ mixture, to an inhaler designed to mix gas from two sources. By controlling the flow of gas from each source, the concentration of NO inhaled by the patient can be maintained at an optimal level. NO can also be mixed with room air, using a standard low-flow blender (e.g., Bird Blender, Palm Springs, Calif.). NO can be generated from $N_2$ and $O_2$ (i.e., air) by using an electric NO generator. A suitable NO generator is described in Zapol, U.S. Pat. No. 5,396,882. In addition, NO can be provided intermittently from an inhaler equipped with a source of NO such as compressed NO or an electric NO generator. The use of an inhaler may be particularly advantageous if a second compound (e.g., a phosphodiesterase inhibitor) is administered, orally or by inhalation, in conjunction with the NO.

NO can be administered to a mammal identified as having a non-pulmonary ischemia-reperfusion injury or inflammation, or a mammal identified as being at risk for developing a non-pulmonary ischemia-reperfusion injury or inflammation. Preferably, the NO concentration is 0.1 ppm to 300 ppm in air, pure oxygen, or another suitable gas or gas mixture. The NO can be administered for as long as needed. The concentration can be temporarily increased for short periods of time, e.g., 5 min at 200 ppm NO. This can be done when an immediate effect is desired.

For treatment or prevention of non-pulmonary ischemia-reperfusion injury or inflammation, inhaled NO can be administered by nasal prongs, mask, tent, intra-tracheal catheter or endotracheal tube, for an extended period, i.e., days or weeks. The administration can be continuous, during the extended period. Alternatively, administration can be intermittent during the extended period. The administration of gaseous NO can be via spontaneous or mechanical ventilation.

Assessment of Effects of Inhaled NO

When inhaled NO is administered, it is desirable to monitor the effects of the NO inhalation. Such monitoring can be used, in a particular individual, to verify desirable effects and to identify undesirable side effects that might occur. Such monitoring is also useful in adjusting dose level, duration and frequency of administration of inhaled NO in a given individual.

Other Agents Administered with NO

NO decomposes rapidly by reacting with molecular oxygen to produce nitrite and nitrate. In addition, NO entering the blood is rapidly inactivated by tight binding to hemoglobin. For these reasons, NO has only a short half-life in arterial blood. This means that inhaled NO advantageously avoids systemic vasodilation, an undesirable, potentially dangerous side effect associated with sustained systemic NO release from NO donor compounds such as nitroglycerin.

It may be desirable to prolong the beneficial effects of inhaled NO within leukocytes or platelets, or within cells interacting with the leukocytes or platelets in the lung. In determining how to prolong the beneficial effects of inhaled NO, it is useful to consider that one of the in vivo effects of NO is activation of soluble guanylate cyclase, which stimulates production of cGMP. At least some of the beneficial effects of NO may result from its stimulation of cGMP biosynthesis. Accordingly, in a some embodiments of the invention, a phosphodiesterase inhibitor is administered in conjunction with NO inhalation to inhibit the breakdown of cGMP by endogenous phosphodiesterases.

The phosphodiesterase inhibitor can be introduced into the mammal by any suitable method, including via an oral, transmucosal, intravenous, intramuscular, subcutaneous or intraperitoneal route. Alternatively, the inhibitor can be inhaled by the mammal. For inhalation, the phosphodiesterase inhibitor is advantageously formulated as a dry powder or an aerosolized or nebulized solution having a particle or droplet size of less than 10 $\mu$m for optimal deposition in the alveoli, and may optionally be inhaled in a gas containing NO.

A suitable phosphodiesterase inhibitor is Zaprinast™ (M&B 22948; 2-o-propoxyphenyl-8-azapurine-6-one; Rhone-Poulenc Rorer, Dagenham Essex, UK). Zaprinast™ selectively inhibits the hydrolysis of cGMP with minimal effects on the breakdown of adenosine cyclic-monophosphate in vascular smooth muscle cells (Trapani et al., J Pharmacol Exp Ther 258:269 [1991]; Harris et al., J Pharmacol Exp Ther 249:394 [1989]; Lugnier et al., Biochem Pharmacol 35:1743 [1986]; Souness et al., Br J Pharmacol 98:725 [1989]). When using Zaprinast™ according to this invention, the preferred routes of administration are intravenous or oral. The suitable dose range may be determined by one of ordinary skill in the art. A stock solution of Zaprinast™ may be prepared in 0.05 N NaOH. The stock can then be diluted with Ringer's lactate solution to the desired final Zaprinast™ concentration, immediately before use.

In a preferred embodiment, the NO is administered at 20 ppm in air for 45 min. At the start of the 45 min period, 10 mg of Zaprinast™ per kg body weight is administered over 4 min, followed by a continuous infusion of 0.004 mg/kg/min for the rest of the 45 min period. Alternatively, at the start of the 45 min period, 0.15 mg dipyridamole per kg body weight is administered over 4 min, followed by a continuous infusion of 0.004 mg/kg/min for the rest of the 45 min period. The Zaprinast™ or dipyridamole are administered in a saline solution. In addition, the methods are not limited to co-administration of only one drug. For example, the administration of either phosphodiesterase inhibitor above can be augmented by administration of a superoxide dismutase.

This invention can be practiced with other phosphodiesterase inhibitors. Various phosphodiesterase inhibitors are known in the art, including dipyridamole and theophylline.

A suitable route of administration and suitable dose range can be determined by one of ordinary skill in the art.

Antithrombotic agents can be administered together with NO in according to the invention. Such antithrombotic agents serve to (1) restore perfusion of the tissues susceptible to ischemia-reperfusion injury via thrombolysis, and (2) augment the therapeutic effects of inhaled NO by decreasing the potential for activiation of platelets in non-pulmonary tissues. Examples of antithrombotic agents are aspirin, streptokinase, urokinase, tissue plasminogen activator ("t-PA"), met-t-PA (i.e., t-PA with an N-terminal methionine residue), FE1X (a t-PA analog), heparin, hirudin, Hirulog™ (a hirudin analog), ticlopidine, and IIb/IIIa (e.g. Rheopro™). Other antithrombotic agents could also be used in the practice of this invention. One or more such antithrombotic agents may be administered to a mammal before, during, or after treatment with inhaled NO, so that the potential of platelets to become activated in non-pulmonary tissues is decreased.

In addition, one or more anti-leukocyte agents (e.g., anti-leukocyte antibodies) can be administered in the methods of this invention. Such agents can be administered with inhaled NO with or without antithrombotic agents. When both anti-leukocyte agents and antithrombotic agents are administered along with NO, such agents can augment the therapeutic effect of NO by further decreasing the potential activation of both leukocytes and platelets in the non-pulmonary tissue susceptible to ischemia-reperfusion injury or inflammation.

The selection of appropriate antithrombotic and/or anti-leukocyte agents to be administered in conjunction with inhaled NO, and the selection of the appropriate dosage and route of administration of those antithrombotic agents, is within ordinary skill in the art.

What is claimed is:

1. A method for treating non-pulmonary ischemia-reperfusion injury in a mammal, comprising the steps of:
   (a) identifying a mammal that has ischemia-reperfusion injury in a non-pulmonary tissue; and
   (b) causing the mammal to inhale a therapeutically effective amount of gaseous nitric oxide sufficient to diminish the ability of the mammal's leukocytes or platelets to become activated in a manner that contributes to an inflammatory process at the site of the ischemia-reperfusion in the non-pulmonary tissue, and
   (c) administering to the mammal a therapeutically effective amount of a second compound that potentiates the therapeutic effect of gaseous nitric oxide.

2. The method of claim 1, wherein the second compound is selected from the group consisting of a phosphodiesterase inhibitor and superoxide dismutase.

3. The method of claim 2, wherein the phosphodiesterase inhibitor is selected from the group consisting of 2-o-propoxyphenyl-8-azapurin-6-one, dipyridamole, theophylline, sildenafil, and 1,3-dimethyl-6-(2-propoxy-5-methanesulphonylamidophenyl)-pyrazolo[3,4-D]pyrimidin-4-(5H)-one.

4. The method of claim 1, wherein the second compound is selected from the group consisting of ticlopidine, streptokinase, urokinase, t-PA and analogs thereof, heparin, and hirudin and analogs thereof.

5. The method of claim 1, wherein the ischemia-reperfusion injury is caused by surgery.

6. The method of claim 5, wherein the surgery is transplantation surgery.

7. The method of claim 6, wherein the transplantation surgery is kidney transplantation surgery or heart transplantation surgery.

8. The method of claim 5, wherein the surgery is heart bypass surgery.

9. The method of claim 1, wherein the ischemia-reperfusion injury is caused by a stroke.

10. The method of claim 1, wherein the ischemia-reperfusion injury occurs in the kidney.

11. The method of claim 1, wherein the ischemia-reperfusion injury occurs in the brain.

12. The method of claim 1, wherein the therapeutically effective amount of nitric oxide is administered to the mammal at a predetermined concentration range.

13. The method of claim 12, wherein the concentration range is 0.1 ppm to 300 ppm.

14. The method of claim 1, wherein the nitric oxide is inhaled continuously for an extended period.

15. The method of claim 1, wherein the nitric oxide is inhaled intermittently for an extended period.

16. The method of claim 1, wherein the mammal is a human.

* * * * *

UNITED STATES PATENT AND TRADEMARK OFFICE
CERTIFICATE OF CORRECTION

PATENT NO. : 6,656,452 B1  Page 1 of 1
APPLICATION NO. : 08/971003
DATED : December 2, 2003
INVENTOR(S) : Warren M. Zapol, Kenneth D. Bloch and Anthony Rosenzweig It is certified that error appears in the above-identified patent and that said Letters Patent is hereby corrected as shown below:

<u>Cover page, left column,</u>
Inventors, after "Kenneth D. Bloch, Brookline, MA (US)" insert
-- ; Anthony Rosenzweig, Newton, MA (US) --

<u>Cover page, right column,</u>
Schmidt et al., "Work" and before "," delete -- K --

Signed and Sealed this

Twenty-sixth Day of February, 2008

JON W. DUDAS
*Director of the United States Patent and Trademark Office*